United States Patent [19]

Rockwell

[11] 4,372,324
[45] Feb. 8, 1983

[54] ANALOG PEAK VOLTAGE DETECTOR IN A DEFIBRILLATOR

[75] Inventor: Martin G. Rockwell, McMinnville, Oreg.

[73] Assignee: Hewlett-Packard Company, Palo Alto, Calif.

[21] Appl. No.: 293,649

[22] Filed: Aug. 17, 1981

[51] Int. Cl.³ .............................................. A61B 5/04
[52] U.S. Cl. ............................... 128/695; 128/419 D
[58] Field of Search ........ 128/695, 696, 697, 702–706, 128/708, 419 D, 902

[56] References Cited

U.S. PATENT DOCUMENTS

| | | | |
|---|---|---|---|
| 3,442,269 | 5/1969 | Druz | 128/419 D |
| 3,747,605 | 7/1973 | Cook | 128/419 D |
| 3,939,824 | 2/1976 | Arneson et al. | 128/708 |
| 3,991,365 | 11/1976 | Takeuchi | 128/695 |

*Primary Examiner*—William E. Kamm
*Attorney, Agent, or Firm*—Stephen P. Fox

[57] ABSTRACT

A circuit for detecting and holding the peak voltage of an analog signal is provided. A constant current source controlled by a digital voltage comparator charges a capacitor. The capacitor is charged to a voltage value equivalent to the peak voltage of the analog signal. By selecting the value of the capacitor and the amplitude of the constant current from the current source, slew rate limiting can be achieved, giving the circuit high noise immunity.

6 Claims, 5 Drawing Figures

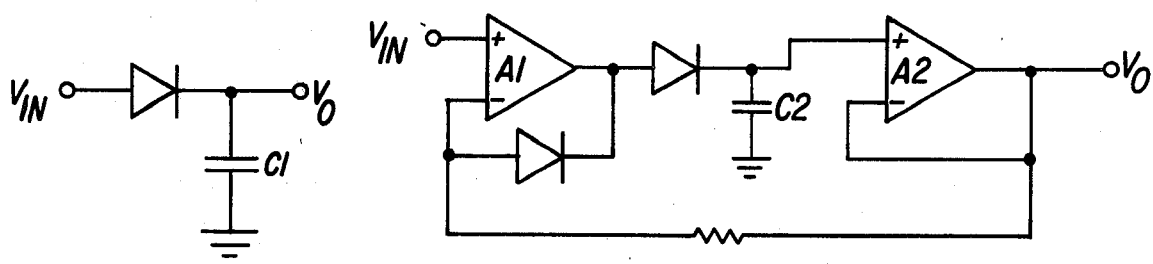
FIGURE 1
(PRIOR ART)
FIGURE 2
(PRIOR ART)
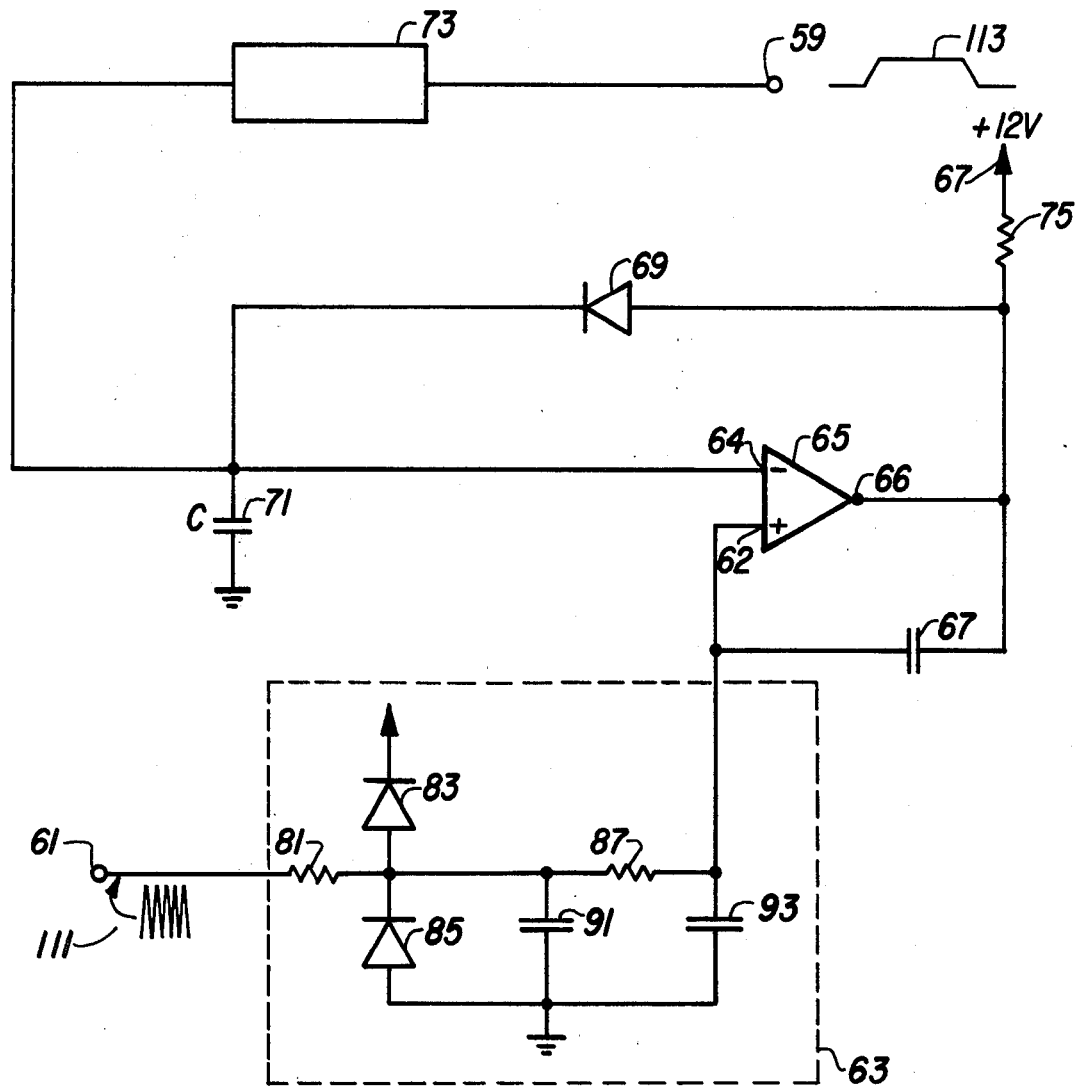
FIGURE 3

ANALOG PEAK VOLTAGE DETECTOR IN A DEFIBRILLATOR

BACKGROUND

The present invention relates to measuring and holding the peak voltage of a signal in a high noise environment. It has been developed to aid the measurement of delivered energy and thoracic impedance of a patient during defibrillation. Since a defibrillator generates an extreme amount of noise during operation, the requirements for a circuit to detect and hold a peak voltage, i.e. a peak detector, include high noise immunity as well as high precision. Heretofore known peak detectors do not adequately fulfill the high noise immunity requirement.

One type of known peak detector circuit is illustrated in FIG. 1. The peak voltage of an analog input signal $V_{in}$ is held in a capacitor C1. There is a voltage drop across a diode D1, which causes capacitor C1 to be undercharged. This limits the accuracy of the circuit. Additionally, the circuit operates over a very wide bandwidth so there is little noise immunity.

Another known peak detector is shown in FIG. 2. The peak value of input signal $V_{in}$ is held in capacitor C2. This circuit has a large amount of negative feedback which gives it high precision. Slew rate limiting can be achieved within first amplifier A1 to mitigate the effect of noise impulses; however in this case, large differential voltages appear across the input nodes of amplifier A1 which may cause the input transistors of amplifier A1 to saturate. A delay in switching off amplifier A1 due to the saturation will cause capacitor C2 to overcharge. This can result in a significant error in the measurement of the peak value of the input voltage.

SUMMARY OF THE INVENTION

In accordance with the preferred embodiment of the present invention there is provided a circuit for detecting and holding the peak voltage of an analog signal. The peak voltage is proportional to peak current through a patient during defibrillation. A constant current source controlled by a digital voltage comparator charges a capacitor. The comparator monitors the analog signal. When the voltage amplitude of the analog signal is greater than the voltage held in the capacitor, the current source is turned on, charging the capacitor. Otherwise the current source is turned off. The resulting voltage across the capacitor is the peak voltage of the analog signal. By selecting the value of the capacitor and the amplitude of the constant current from the current source, slew rate limiting can be achieved, giving the circuit high noise immunity.

BRIEF DESCRIPTION OF THE DRAWINGS

FIG. 1 and FIG. 2 are schematic circuits illustrating prior art voltage peak detectors.

FIG. 3 is a schematic circuit diagram of one embodiment of the present invention.

DESCRIPTION OF THE PREFERRED EMBODIMENT

Figure 4:
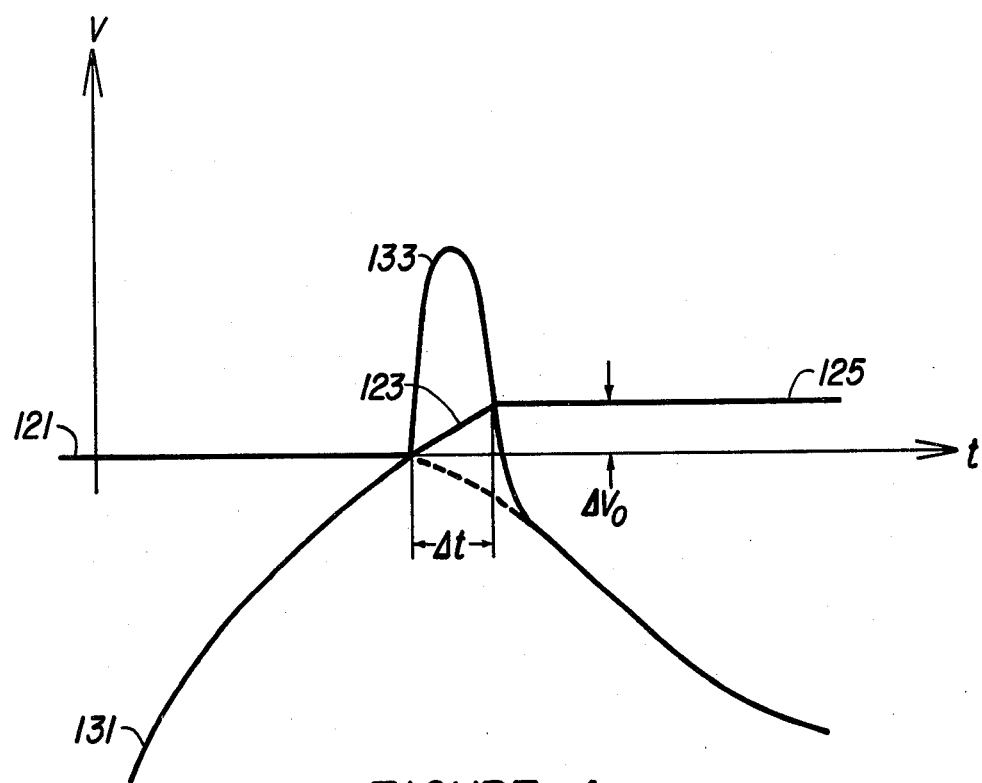
FIG. 4 is a graph of voltage vs. time illustrating certain operational features of the circuit of FIG. 3.

Referring now to FIG. 3, an input signal 111 is applied to a circuit input node 61. Input node 61 is coupled to an input filter 63. Input filter 63 includes an input resistor 81 which is coupled to a diode 83 to limit the maximum voltage of signal 111, and to a diode 85 to limit the minimum voltage of signal 111. Filter 63 also includes a two-pole low pass filter including a capacitor 91 and 93, each having one lead coupled to ground and the other lead coupled to opposite ends of a resistor 87. The low pass filter is coupled at the junction of capacitor 91 and resistor 87 to input resistor 81.

Input filter 63 is coupled at the junction of resistor 87 and capacitor 93 to a positive input node 62 of a comparator 65. Comparator 65 includes metal oxide silicon field effect transistor (MOSFET) circuitry (not shown) coupled to positive input node 62 and a negative input node 64. MOSFET circuitry is chosen because it provides the comparator with high input impedance. Comparator 65 also has an output node 66. In the output circuitry of comparator 65 there is no collector resistance, i.e. comparator 65 has an open collector output. This allows output node 66 to be coupled to ground. Comparator 65 is turned on when positive input node 62 is at a higher voltage than negative input node 64. Output node 66 is coupled to ground when comparator 65 is turned off, and acts as an infinite impedance when comparator 65 is turned on. A positive feedback capacitor 67 may be attached between input node 62 and output node 66 in order to prevent undesirable comparator oscillation.

A resistor 75 is coupled between a constant voltage power source 67 set at 12 volts, and output node 66. Resistor 75 and power source 67 act to produce a constant current source at the junction of resistor 75 and output node 66. A capacitance 71 is coupled to the constant current source through a diode 69. More particularly, the anode of diode 69 is attached to output node 66, and the cathode is connected to capacitor 71. Diode 69 acts as a switch for the constant current source to pass current to capacitor 71 when comparator 65 is turned on, and to cut off current flow when comparator 65 is turned off. The capacitor acts as a capacitive storage device to store the peak voltage value of analog signal 111, as described in more detail hereinafter.

Coupled also to the junction of capacitor 71 and input node 64 is a buffer amplifier 73. Buffer amplifier 73 has high input impedance, low output impedance and a gain of one. Coupled to buffer amplifier 73 is an output node 59.

Overall circuit operation is as follows: Input signal 111 enters the circuit at input node 61. Input filter 63 filters signal 111 before it reaches comparator 65. Comparator 65 compares the voltage of the filtered signal at input node 62 with a voltage value across capacitor 71. Initially there is no bias across capacitor 71. If the voltage of signal 111 is higher than the voltage value across capacitor 71, the comparator is turned on, i.e. the comparator output node acts as an infinite impedance. Power source 67 pulls the voltage at output node high, causing diode 69 to be forward biased. A substantially constant current is conducted from power source 67 through resistor 75 and diode 69. This current charges capacitor 71, increasing the voltage across capacitor 71.

When the voltage of signal at node 62 is lower than the voltage across capacitor 71, comparator 65 is turned off, i.e. the output node acts as a current sink set at ground. The voltage at output node 66 is grounded, back biasing diode 69. This switches the current off. The resulting voltage stored across capacitor 71 is the peak voltage of signal 111. Buffer amplifier 73 delivers the value of the peak voltage to output node 59 as an output signal 113.

It can be seen that diode 69 acts as a switch for the constant current source consisting of power source 67 and resistor 75. Comparator 65 digitally controls diode 69, causing the constant current source to be turned on when comparator 65 is on and off when comparator 65 is off. The switching of the current source on and off results in constant current pulses being sent to capacitor 71. The duration of a pulse is the length of time from the time capacitor 65 turns on until it turns off.

The circuit elements of FIG. 3 can be selected to increase noise immunity. An example of how the peak detector achieves slew rate limiting to decrease the adverse effect of circuit noise is illustrated in FIG. 4.

A voltage level 121 is held across capacitor 71 (FIG. 3). A voltage signal 131 enters the circuit at node 61 (FIG. 3). A random noise spike 133 hypothetically occurs when voltage signal 131 reaches its peak value. The voltage level 121 across capacitor 71 increases at a slew rate 123 to a final voltage level 125.

Slew rate 123 can be varied, for instance, by adjusting the values of capacitor 71 and resistor 75 (FIG. 3). For a time duration $\Delta t$ of noisepike 133 a change in voltage $\Delta Vo$ between final voltage value 125 and initial voltage value 121 can be calculated by:

$$\Delta Vo = (Io/C) \times \Delta t$$

where Io is the constant current through resistor 75 (FIG. 3) and C is the value of capacitor 71. Slew rate 123 can be calculated by:

Slew rate 123 = $\Delta Vo/\Delta t$

Assume that time duration $\Delta t$ is 1 microsecond ($\mu S$), resistor 75 is chosen to be 5 kilohm (resulting in constant current Io being approximately equal to 2.5 milliamps (mA)) and capacitor 71 is chosen to be 0.33 microfarads ($\mu F$). Then:

$$\Delta Vo = (2.5 mA/.33\ \mu F) \times 1\ \mu S$$
$$= 7.6 \text{ millivolts (mV)},$$

and $$\text{slew rate } 123 = (7.6\ mV)/(1\ \mu S)$$
$$= 7.6\ mV/\mu S$$
$$= 7.6 \text{ kilovolts per second}$$

The above given example approximates the conditions within a defribrillator. Typically analog signal 111 will vary in voltage amplitude from zero to five volts, and in frequency up to 900 Hertz. Noise spikes vary widely in amplitude and in frequency from 1 kilohertz to several gigahertz. The actual voltage difference $\Delta Vo$ resulting in this case, i.e. 7.6 millivolts, is negligible for the calculation of peak voltage in a defibrillator.

Figure 5:
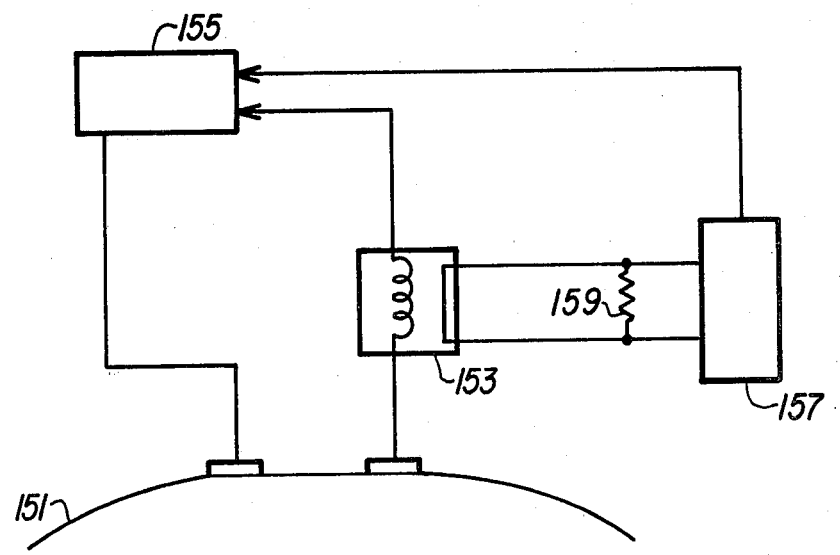
FIG. 5 is a block diagram illustrating an application of a peak voltage detector in a defibrillator circuit.

Referring now to FIG. 5, the chest of a patient 151 is coupled to defibrillator circuits 155 through a transformer 153. A peak voltage detector 157 is coupled to transformer 153 and defibrillator circuits 155. When defibrillator circuits 155 deliver a current to patient 151, transformer 153 transforms the current into a proportional current. The proportional current is channelled through a load resistance 159 to deliver a voltage to peak detector 157 that is proportional to the defibrillator current. Peak detector 157 determines the peak value of the proportional voltage and delivers it to defibrillator circuits 155. The peak value of the proportional voltage indicates to defibrillator circuits 155 the maximum current delivered to patient 151. The value of the maximum current may be used by the defibrillator circuits in the calculation of selected parameters such as the thoracic impedance through patient 151 and the electrical energy delivered to patient 151 during defibrillation.

I claim:

1. An apparatus for detecting the maximum current conducted through a patient during defibrillation comprising:

current generating means for generating a substantially constant current;

switching means coupled to the current generating means for switching the current generating means on and off;

capacitive storage means coupled to an output of the current generating means for storing a held voltage and increasing the held voltage at a substantially constant rate while the current generating means is turned on;

transforming means coupled to the patient for transforming the current through the patient to a proportional voltage; and voltage comparison means coupled to the capacitive storage means, the transforming means, and the switching means, for causing the switching means to turn the current generating means on when the held voltage is less than said proportional voltage and off when the held voltage is greater than said proportional voltage, thereby increasing the held voltage until it is equal to the maximum value of the proportional voltage thereby indicating the maximum current conducted through the patient.

2. An apparatus as in claim 1 wherein the voltage comparison means includes a voltage comparator with an open collector output, the switching means includes a diode, the capacitive storage means includes a capacitor, and the current generating means includes a resistance coupled to a voltage source.

3. An apparatus for detecting the peak voltage of an analog signal comprising:

current generating means for generating a substantially constant current;

switching means coupled to the current generating means for switching the current generating means on and off;

capacitive storage means coupled to an output of the current generating means for storing a held voltage and increasing the held voltage at a substantially constant rate while the current generating means is turned on; and voltage comparison means having an input node for receiving the analog signal, and having an output node coupled to the capacitive storage means and to the switching means, for causing the switching means to turn the current generating means on when the held voltage is less than the voltage of the analog signal and off when the held voltage is greater than the voltage of the analog signal, thereby increasing the held voltage until it is equal to the peak voltage of the analog signal.

4. An apparatus as in claim 3 further including buffering means coupled to the capacative storage means, for buffering the held voltage to a circuit output node.

5. An apparatus as in claim 4 further including means for filtering a signal applied to the input node.

6. An apparatus as in claim 5 wherein the voltage comparison means includes a voltage comparator with an open collector output, the switching means includes a diode, the capacitive storage means includes a capacitor, and the current generating means includes a resistance coupled to a voltage source.

* * * * *

UNITED STATES PATENT AND TRADEMARK OFFICE
CERTIFICATE OF CORRECTION

PATENT NO. : 4,372,324

DATED : February 8, 1983

INVENTOR(S) : Martin G. Rockwell

It is certified that error appears in the above-identified patent and that said Letters Patent are hereby corrected as shown below:

Column 3, line 12, delete "capacitor" and substitute -- comparator --;

Column 3, line 25, delete "noisepike" and substitute -- noisespike --.

Signed and Sealed this

Twelfth Day of April 1983

[SEAL]

Attest:

GERALD J. MOSSINGHOFF

Attesting Officer    Commissioner of Patents and Trademarks